United States Patent [19]
Hostalek et al.

[11] Patent Number: 5,234,716
[45] Date of Patent: Aug. 10, 1993

[54] ORGANOMETALLIC ADDUCT COMPOUNDS

[75] Inventors: Martin Hostalek, Darmstadt; Matthias Lokai, Enkenbach-Alsenborn; Ludwig Pohl, Darmstad, all of Fed. Rep. of Germany

[73] Assignee: Merck Patent Gesellschaft mit Beschraenkter Haftung, Darmstadt, Fed. Rep. of Germany

[21] Appl. No.: 752,698

[22] PCT Filed: Mar. 3, 1990

[86] PCT No.: PCT/EP90/00357
  § 371 Date: Sep. 6, 1991
  § 102(e) Date: Sep. 6, 1991

[87] PCT Pub. No.: WO90/10727
  PCT Pub. Date: Sep. 20, 1990

[30] Foreign Application Priority Data
  Mar. 9, 1989 [DE] Fed. Rep. of Germany ..... 93907581

[51] Int. Cl.$^5$ .............................................. C23C 16/00
[52] U.S. Cl. .................... 427/255.6; 556/1; 556/20; 556/30; 556/174; 536/176
[58] Field of Search .......... 427/248.1, 255.6; 556/1, 20, 30, 174, 176

[56] References Cited
FOREIGN PATENT DOCUMENTS

| 0080349 | 6/1983 | European Pat. Off. |
| 0080844 | 6/1983 | European Pat. Off. |
| 0251555 | 1/1988 | European Pat. Off. |
| 8603228 | 6/1986 | PCT Int'l Appl. |

OTHER PUBLICATIONS

M. Schirmaier et al., "Low Pressure Deposition of GaAs from Triethylgallium-diisopropylamin-adduct and Arsine," GaAs & Related Compounds, Seattle, 1991, Abstract and Summary.

Long, J. A. et al., *Growth of Fe-Doped Sonic Insulating InP by MOCVD*, Journal of Crystal Growth 69 (1984), pp. 10-14.

Maury, F. et al., *Mass Spectrometric Study of the Pyrolysis of Organometallic Precursors Usable in GaAs Vapor Phase Epitaxy*, Journal of Crystal Growth 91 (1988) pp. 97-104.

Bradley, Donald C. et al., *The Volatilities of Some Adducts of Trimethyl Indian*, Journal of Crystal Growth 92 (1988) pp. 37-45.

Primary Examiner—Michael Lusigan
Attorney, Agent, or Firm—Millen, White, Zelano & Branigan

[57] ABSTRACT

The invention relates to the use of stabilised organometallic adduct compounds for the production of thin films and epitaxic layers by gas phase deposition.

10 Claims, No Drawings

ORGANOMETALLIC ADDUCT COMPOUNDS

The invention relates to the use of organometallic adduct compounds containing, as metals, aluminium, gallium or indium, for the production of thin films or of epitaxic layers by gas phase deposition, and to new adducts containing gallium or indium.

The deposition of such layers either from pure elements of the third group or from combinations with other elements, such as, for example, gallium arsenide, indium phosphide or gallium phosphide, can be used for the production of electronic and optoelectronic switching elements, compound semiconductors and lasers. The deposition of these layers is effected from the gas phase.

The properties of these films depend on the deposition conditions and on the chemical composition of the film deposited.

All the known methods, such as the metal-organic chemical vapour deposition (MOCVD) method, the photo-metal-organic vapour phase (photo-MOVP) method in which the substances are decomposed by UV irradiation, the laser-chemical vapour deposition (laser CVD) method or the metal-organic magnetron scattering (MOMS) method, are suitable for deposition from the gas phase. The advantages compared with other methods are a controllable growth of the layer, an accurate doping control and also easy handling and convenience of production because of the normal pressure or low-pressure conditions.

In the MOCVD method organometallic compounds which decompose at a temperature below 1100° C. with deposition of the metal are employed. Typical apparatus used at present for MOCVD consists of a "bubbler" having a feeder for the organometallic component, a reaction chamber containing the substrate to be coated and a source of a carrier gas which should be inert towards the organometallic component. The "bubbler" is kept at a constant, relatively low temperature which is preferably above the melting point of the organometallic compound, but far below its decomposition temperature. The reaction chamber or decomposition chamber is preferably at a very much higher temperature, which should be below 1100° C., at which the organometallic compound is completely decomposed and the metal is deposited. The organometallic compound is brought into the vapour state by means of the carrier gas and is admitted into the decomposition chamber together with the carrier gas. The mass flow of the vapour can be controlled easily and thus controlled growth of the thin layers is also possible.

Hitherto metal alkyls, such as, for example, trimethylgallium, trimethylaluminium or trimethylindium, have been mainly used for gas phase deposition. However, these compounds are extremely sensitive to the air and self-ignitable and in some cases can decompose even at room temperature. Involved precautions are therefore necessary for the preparation, transport, storage and use of these compounds. Some rather more stable adducts of metal alkyls with Lewis bases, such as, for example, trimethylamine and triphenylphosphine, are also known (for example are described in British Patent 2,123,422, EP-A 108,469 or EP-A 176,537), but these have only a limited suitability for gas phase deposition because of their low vapour pressure.

However, in contrast with the adduct compounds to be used in accordance with the invention, these known adducts do not contain hydrogen atoms as a radical on the V element.

Organometallic compounds suitable for the MOCVD technique are known from German Offenlegungsschrift 3,631,469. The compounds described therein are, however, not adducts, but compounds which have been stabilised within the molecule.

It was therefore the object of the present invention to find organometallic adduct compounds which are simple to handle and stable at room temperature and which have a sufficiently high vapour pressure to be enabled to decompose from the gas phase and are consequently suitable for the various methods of gas phase deposition.

It has now been found that organometallic adduct compounds of the third and fifth main group, the compound of the fifth main group containing one or two hydrogen atoms, are excellently suitable for gas phase deposition.

These adducts have a decisive advantage over the organometallic adducts hitherto used and known, which have the structure $R_3MXR_3$ and thus contain only alkyl or aryl groups.

The adducts according to the invention, which have at least one H atom on the element of the fifth main group, react at fairly high temperatures ($>100°$ C.) with the release of $R^*H$ ($R^*$ being $R^1$, $R^2$ or $R^3$) to give compounds of the structure $R^*_2MXR^4R^5$. In these compounds the MX bond can be regarded as weak compared with the groups attached to the metal of the third main group, and thus the group $XR^4R^5$ constitutes a very good detachable group. In the MOCVD process, therefore, the substance $R^*_2MXR^4R^5$ produced in situ on the hot wafer leads to a reduced incorporation of carbon.

Stabilised adducts of this type have in part been described, but only in connection with structural investigations, investigations of complex formation or stability investigations. In part, the compounds of the formula I are also new.

The invention therefore relates to the use of organometallic adduct compounds of the formula I

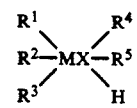

wherein M is aluminium, gallium or indium, X is nitrogen, phosphorus, arsenic or antimony, $R^1$, $R^2$, $R^3$ and $R^4$ independently of one another are each H, an alkyl group which has 1–8 C atoms and which can also be partly or completely fluorinated, a cycloalkyl, alkenyl or cycloalkenyl group having 3–8 C atoms in each case or an aryl group, and $R^5$ is an alkyl group which has 1–8 C atoms and which can also be partly or completely fluorinated, a cycloalkyl, alkenyl or cycloalkenyl group having 3–8 C atoms in each case or an aryl group, as starting materials for the production of thin films or epitaxic layers by gas phase deposition and to a process for the preparation of thin films or epitaxic layers by gas phase deposition from organometallic compounds, in which process the organometallic compounds employed are the compounds of the formula I. The invention also relates to the introduction, in the process according to the invention, of one or more compounds of arsenic, antimony or phosphorus which are gaseous under the reaction conditions used, in the course of the deposition process.

The invention also relates to the new adducts of the formula I corresponding to the formula II

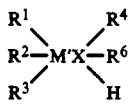

wherein M' is gallium or indium, X is nitrogen, phosphorus, arsenic or antimony, $R^1$, $R^2$, $R^3$ and $R^4$ independently of one another are each H, an alkyl group which has 1-8 C atoms and which can also be partly or completely fluorinated, a cycloalkyl, alkenyl or cycloalkenyl group having 3-8 C atoms in each case, or an aryl group and $R^6$ is a branched alkyl group which has 3-8 C atoms and which can be partly or completely fluorinated.

The stability of the adducts of the formulae I and II is based on the transfer of electrons from the nitrogen, phosphorus, arsenic or antimony atom onto the electron-deficient IIIB element. These adducts therefore display a high stability to air and oxygen, they are no longer self-ignitable and they are therefore easy to handle.

In the gas phase, however, the compounds according to the invention can be decomposed readily with deposition of the metal. Since the compounds of the formulae I and II contain stable detachable groups which can be split off readily, the result is a lower incorporation of carbon, which has great advantages for the quality of the end products.

The films deposited can be formed either from the pure IIIB element or from a combination with elements of the fifth group, on any desired substrates. Depending on the substrate and the deposition technique, they can be of an epitaxic nature. Many of the adducts of the formulae I and II are therefore also particularly suitable for the MOCVD method, since they are present as monomers and therefore in most cases as liquids at room temperature.

The adducts of the formulae I and II have a vapour pressure which is suitable for the MOCVD technique and they are therefore excellently suitable for use as starting materials.

In the formula I, M is aluminium (Al), gallium (Ga) or indium (In), preferably Ga or In.

The new adducts of the formula II wherein M' is Ga or In are particularly preferred compounds of the formula I.

X in the formulae I and II is nitrogen as a first preference or phosphorus or arsenic as a second preference.

The radicals $R^1$, $R^2$, $R^3$ and $R^4$ in the formulae I and II are preferably each H or a linear or branched alkyl group having 1-8 C atoms, preferably 1-5 C atoms. The alkyl groups are preferably linear and accordingly are preferably methyl, ethyl, propyl, butyl, pentyl and also hexyl, heptyl, octyl, isopropyl, sec.-butyl, tert.-butyl, 2-methylpentyl, 3-methylpentyl or 2-octyl. The alkyl radicals can be partly or completely fluorinated and are, for example, monofluoromethyl, trifluoromethyl, difluoroethyl, trifluoroethyl, pentafluoroethyl or trifluoropropyl. Preferably, only one of the radicals $R^1$, $R^2$, $R^3$ or $R^4$ is H.

If $R^1$, $R^2$, $R^3$ and/or $R^4$ are a cycloalkyl or cycloalkenyl group having 3-8 C atoms, they are preferably cyclopropyl, cyclobutyl, cyclopentyl, cyclopentenyl, cyclohexyl, cyclohexenyl, cyclohexadienyl, cycloheptyl, cycloheptenyl, cycloheptadienyl, cyclooctyl, cyclooctenyl, cyclooctadienyl, cyclooctatrienyl or cyclooctatetraenyl.

$R^1$, $R^2$, $R^3$ and/or $R^4$ are preferably also alkenyl groups having 3-8 C atoms, preferably 3-5 C atoms. Accordingly they are preferably propenyl, butenyl, pentenyl and also hexenyl, heptenyl or octenyl.

Furthermore, compounds of the formulae I and II wherein $R^1$, $R^2$, $R^3$ and/or $R^4$ are an aryl group are preferred. In this regard aryl is preferably synonymous with a phenyl group. This phenyl group can also contain substituents. Since these substituents exert no appreciable effect on the desired end use, any substituents which have no interfering effect on the decomposition reaction are allowed.

$R^5$ in formula I is preferably an alkyl group having 1-8 C atoms, preferably 1-5 C atoms. It can be linear or branched, but is preferably branched and, accordingly, is preferably isopropyl, sec.-butyl, tert.-butyl and also preferably 2-methylpentyl, 3-methylpentyl, 2-octyl, methyl, ethyl, propyl, butyl, hexyl, heptyl or octyl.

The alkyl radical in R: can also be partly or completely fluorinated and is then preferably monofluoromethyl, trifluoromethyl, difluoroethyl, trifluoroethyl, pentafluoroethyl or trifluoropropyl.

If $R^5$ is a cycloalkyl or cycloalkenyl group or an alkenyl group, preferred groups are those which are also indicated as preferred for $R^1$-$R^4$.

$R^6$ in formula II is a branched alkyl group which has 3-8 C atoms, preferably 3-5 C atoms, and which can also be partly or completely fluorinated. $R^6$ is, accordingly, preferably isopropyl, sec.-butyl, tert.-butyl, 1-methylbutyl, 2-methylbutyl, 1,2-dimethylpropyl and also 2-methylpentyl, 3-methylpentyl, 2-octyl or 2-hexyl.

The new adducts of the formula II thus contain at least one branched alkyl group and at least one hydrogen atom in the moiety containing the element of the fifth group.

Compounds of the formula II belonging to the following groups are particularly preferred:
(methyl)$_3$ Ga NH (isopropyl)$_2$
(ethyl)$_3$ Ga NH (isopropyl)$_2$
(methyl)$_3$ In NH (isopropyl)$_2$
(ethyl)$_3$ In NH (isopropyl)$_2$
(methyl)$_3$ Ga-AsH$_2$ (isopropyl)
(methyl)$_3$ Ga-AsH (isopropyl)$_2$
(ethyl)$_3$ Ga-AsH$_2$ (tert.-butyl)
(ethyl)$_3$ Ga-NH (sec.-butyl)$_2$
$R^1R^2R^3$ Ga NH$_2$ (tert.-butyl)
$R^1R^2R^3$ Ga NH$_2$ (2-octyl)
$R^1R^2R^3$ Ga NH$_2$ (2-methylpentyl)
$R^1R^2R^3$ In PH (isopropyl)$_2$
$R^1R^2R^3$ In PH$_2$ (isopropyl)
$R^1R^2R^3$ In PH (sec.-butyl)$_2$
$R^1R^2R^3$ In PH (tert.-butyl)$_2$
$R^1R^2R^3$ In PH$_2$ (3-methylpentyl)
$R^1R^2R^3$ In NH$_2$ (tert.-butyl)
$R^1R^2R^3$ In NH (2-octyl)$_2$ These compounds are also preferred adducts of the formula I. The following are further preferred adducts of the formula I:
(methyl)$_3$ Al NH (ethyl)$_2$
(methyl)$_3$ Al NH$_2$ (ethyl)
(ethyl)$_3$ Al NH (ethyl)$_2$
(ethyl)$_3$ Al NH (isopropyl)$_2$ (methyl)₃ Al NH (cyclohexyl)₂
(propyl)₃ Al NH₂ (methyl)
(ethyl)₃ Ga NH (ethyl)₂
(ethyl)₃ In NH (methyl)₂
(ethyl)₃ Ga NH₂ (phenyl)
(ethyl)₃ Ga AsH (pentyl)₂
(methyl)₃ Ga AsH₂ (butyl)
(isopropyl)₃ In PH (ethyl)₂
(ethyl)₃ In PH (phenyl)₂.

The compounds of the formulae I and II are excellently suitable for MOCVD epitaxy or the MOCVD method, since they decompose at elevated temperatures with liberation of the corresponding metal. They are also suitable for the other methods of gas phase deposition, such as photo-MOVP, laser-CVD or MOMS.

The compounds of the formulae I and II are prepared by methods known per se, such as are described in the literature (for example G. Bähr, P. Burba, Methoden der organischen Chemie ("Methods of organic chemistry"), Volume XIII/4, Georg Thieme Verlag, Stuttgart (1970)), specifically under reaction conditions which are known and suitable for the reactions mentioned. In this regard it is also possible to make use of variants which are known per se but are not mentioned here in detail.

For example, the adducts can be prepared by direct reaction of appropriate compounds of the III elements ($R^1R^2R^3M$ or $R^1R^2R^3M'$) with the compounds containing the element of the fifth group ($XHR^4R^5$ or $XHR^4R^6$). Another possible means is to react an appropriate ether derivative of the III compound with the fifth compound, in the course of which a ligand exchange takes place (for example the exchange already described by G. Bähr, P. Burba, Houben-Weyl, Volume 13/4, page 338, Georg Thieme Verlag, Stuttgart (1970)).

In the process according to the invention for the production of thin films or epitaxic layers on any desired substrates, the stabilised organometallic adduct compounds of the formula I are employed as starting compounds in the gas phase deposition processes, known per se, of organometallic compounds. The reaction conditions can be chosen analogously to the values known from the literature and familiar to those skilled in the art.

In order to produce compound semiconductors or electronic and optoelectronic components, one or more compounds of arsenic, antimony or phosphorus which are gaseous under the reaction conditions used, for example $AsH_3$, $As(CH_3)_3$, $PH_3$ or $SbH_3$, can be added in addition, in the process according to the invention, during the deposition process in the decomposition chamber. A further variant of the process according to the invention consists in adding doping agents during the deposition process in addition to the organometallic adducts, according to the invention, of the formula I. Doping agents employed in this regard are volatile organometallic compounds of iron, magnesium, zinc or chromium. Examples of compounds considered to be preferred in this regard are $Zn(CH_3)_2$, $Mg(CH_3)_2$ or $Fe(C_5H_5)_2$.

It is also possible to add the compounds of the formula I as doping agents during the process of depositing other organometallic compounds.

The layers produced by the process according to the invention can be used for the production of electronic and optoelectronic switching elements, compound semiconductors or lasers.

Since only approx. 1–10 % of the free metal alkyls employed can, for thermodynamic reasons, be deposited on the substrate as an epitaxic layer in the epitaxy equipment in use at the present time, the destruction of the excess metal alkyls, which cannot be recovered because of their extreme sensitivity, constitutes a considerable problem. Because of their high stability, however, the compounds, according to the invention, of the formula I open up new possibilities for the safe destruction or recovery of the valuable IIIB compounds.

The following examples are intended to illustrate the invention in greater detail without limiting it. Temperature data are given in degrees centigrade or Kelvin. M.p. means melting point and b.p. means boiling point.

Example 1

270 g (0.27 mol) of diisopropylamine are added to 30.6 g (0.27 mol) of trimethylgallium diethyl etherate. The ether is then removed by distillation and the product is fractionally distilled. This gives (methyl)₃ Ga NH (isopropyl)₂ of b.p. 138° C.

The following are prepared analogously:
(methyl)₃ Ga NH (propyl)₂
(methyl)₃ Ga NH (sec.-butyl)₂
(methyl)₃ Ga NH (tert.-butyl)₂
(methyl)₃ Ga NH₂ (ethyl)
(methyl)₃ Ga NH₂ (isopropyl)
(ethyl)₃ Ga NH (isopropyl)₂
(ethyl)₃ Ga NH (propyl)₂
(ethyl)₃ Ga NH (sec.-butyl)₂
(ethyl)₃ Ga NH (tert.-butyl)₂
(ethyl)₃ Ga NH₂ (methyl)
(ethyl)₃ Ga NH₂ (isopropyl)
(methyl)₃ Ga NH (phenyl)₂

Example 2

(Methyl)₃ In NH(isopropyl)₂ of b.p. 69° at 10 mbar is obtained analogously to Example 1 by reacting 61.0 g (0.26 mol) of trimethylindium diethyl etherate and 101.0 g (0.26 mol) of diisopropylamine at 20°.

The following are prepared analogously:
(methyl)₃ In NH (propyl)₂
(methyl)₃ In NH (ethyl)₂
(methyl)₃ In NH (sec.-butyl)₂
(methyl)₃ In NH (tert.-butyl)₂
(methyl)₃ In NH₂ (ethyl)
(methyl)₃ In NH₂ (isopropyl)
(ethyl)₃ In NH (isopropyl)₂
(ethyl)₃ In NH (propyl)₂
(ethyl)₃ In NH (ethyl)₂
(ethyl)₃ In NH (phenyl)₂
(ethyl)₃ In NH (sec.-butyl)₂
(ethyl)₃ In NH₂ (methyl).

Example 3

Use of the (methyl)₃GaNH(isopropyl)₂ adduct for epitaxy.

The (methyl)₃GaNH(isopropyl)₂ adduct was used for epitaxy together with $AsH_3$ in a low-pressure MOCVD apparatus (1000–2000 Pa). The growth temperatures were between 850° K. and 1050° K. The electron mobility at 77° K. of the GaAs layer produced by epitaxy was $\mu_{77} = 51000$ cm²/Vs. Incorporation of nitrogen was not observed.

We claim:

1. Organometallic adduct compounds of the fomula II

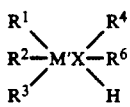

wherein M' is gallium or indium, X is nitrogen, phosphorus, arsenic or antimony, $R^1$, $R^2$, $R^3$ and $R^4$ independently of one another are each H, an alkyl group which has 1-8 C atoms and which can also be partly or completely fluorinated, a cycloalkyl, alkenyl or cycloalkenyl group having 3-8 C atoms in each case, or an aryl group and $R^6$ is a branched alkyl group which has 3-8 C atoms and which can be partly or completely fluorinated.

2. A process for the production of thin films or layers from organometallic adduct compound by gas phase deposition, wherein said organometallic adduct compounds are of the formula I

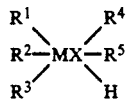

wherein:
M is aluminum, gallium, or indium;
X is nitrogen, phosphorus, arsenic, or antimony;
$R^1$, $R^2$, $R^3$, and $R^4$ are each, independently of each other, H, a $C_{1-8}$-alkyl group, a partly or completely fluorinated $C_{1-8}$-alkyl group, or a $C_{3-8}$-alkenyl group;
$R^5$ is a $C_{1-8}$-alkyl group, a partly or completely fluorinated $C_{1-8}$-alkyl group, or a $C_{1-3}$-alkenyl group.

3. A process according to claim 2, wherein said thin films or layers are epitaxic layers.

4. A process according to claim 2, wherein doping agents are further introduced during said gas phase deposition.

5. A process according to claim 2, wherein said organometallic adduct compound of the formula I is (methyl)$_3$ GaNH(isopropyl)$_2$.

6. A process according to claim 2, wherein said organometallic adduct compound of the formula I is (methyl)$_3$ InNH(isopropyl)$_2$.

7. A process according to claim 2, wherein said organometallic adduct compound of the formula I is (ethyl)$_3$ GaNH(isopropyl)$_2$.

8. In a process for the production of a semiconductor, electronic, or optoelectronic component or a laser, comprising producing a thin film or layer from an organometallic adduct compound by gas phase deposition, the improvement wherein the compound has formula I

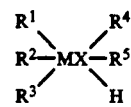

wherein:
M is aluminum, gallium, or indium;
X is nitrogen, phosphorus, arsenic, or antimony;
$R^1$, $R^2$, $R^3$, and $R^4$ are each, independently of each other, H, a $C_{1-8}$-alkyl group, a partly or completely fluorinated $C_{1-8}$-alkyl group, or a $C_{3-8}$-alkenyl group;
$R^5$ is a $C_{1-8}$-alkyl group, a partly or completely fluorinated $C_{1-8}$-alkyl group, or a $C_{1-3}$-alkenyl group, and at least one gaseous compound of arsenic, antimony, or phosphorus is introduced during said gas phase deposition.

9. A process according to claim 8, wherein the at least one compound of arsenic, antimony, or phosphorus is $AsH_3$, $As(CH_3)_3$, or $SbH_3$.

10. A process of producing thin films or layers by gas phase deposition from organometallic adduct compounds, comprising adding doping agents of the formula I

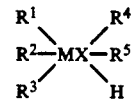

wherein:
M is aluminum, gallium, or indium;
X is nitrogen, phosphorus, arsenic, or antimony;
$R^1$, $R^2$, $R^3$, and $R^4$ are each, independently of each other, H, a $C_{1-8}$-alkyl group, a partly or completely fluorinated $C_{1-8}$-alkyl group, or a $C_{3-8}$-alkenyl group;
$R^5$ is a $C_{1-8}$-alkyl group, a partly or completely fluorinated $C_{1-8}$-alkyl group, or a $C_{1-3}$-alkenyl group.

* * * * *